(12) United States Patent
Heesch et al.

(10) Patent No.: US 8,528,546 B2
(45) Date of Patent: Sep. 10, 2013

(54) MONITORING DEVICE FOR A THERAPY DEVICE AND PROCESS

(75) Inventors: Ralf Heesch, Luebeck (DE); Robert Schmid, Luebeck (DE)

(73) Assignee: Draeger Medical GmbH, Lübeck (DE)

( * ) Notice: Subject to any disclaimer, the term of this patent is extended or adjusted under 35 U.S.C. 154(b) by 0 days.

(21) Appl. No.: 13/457,941

(22) Filed: Apr. 27, 2012

(65) Prior Publication Data

US 2012/0204873 A1 Aug. 16, 2012

Related U.S. Application Data

(62) Division of application No. 11/773,042, filed on Jul. 3, 2007, now abandoned.

(30) Foreign Application Priority Data

Jul. 14, 2006 (DE) .......................... 10 2006 032 860

(51) Int. Cl.
*A61M 16/00* (2006.01)
*F16K 1/08* (2006.01)

(52) U.S. Cl.
USPC .............. 128/200.24; 128/202.22; 128/204.18

(58) Field of Classification Search
None
See application file for complete search history.

(56) References Cited

U.S. PATENT DOCUMENTS

2003/0214409 A1* 11/2003 Hickle ..................... 340/573.1
2005/0010165 A1* 1/2005 Hickle ........................ 604/66

* cited by examiner

*Primary Examiner* — Betty Forman
(74) *Attorney, Agent, or Firm* — McGlew and Tuttle, P.C.

(57) ABSTRACT

A monitoring device for monitoring a therapy device, for example, an anesthesia device or a respirator, is provided by which an alarm device for triggering an alarm when the value drops beyond a warning limit (4) is automatically activated when a determined therapy parameter drops beyond this warning limit (4). The warning limit (4) is set automatically in this case. In addition, a therapy device monitored by the monitoring device and especially an anesthesia device as well as a respirator are provided. A process for triggering an alarm as well as a process for treating a patient is also provided.

10 Claims, 1 Drawing Sheet

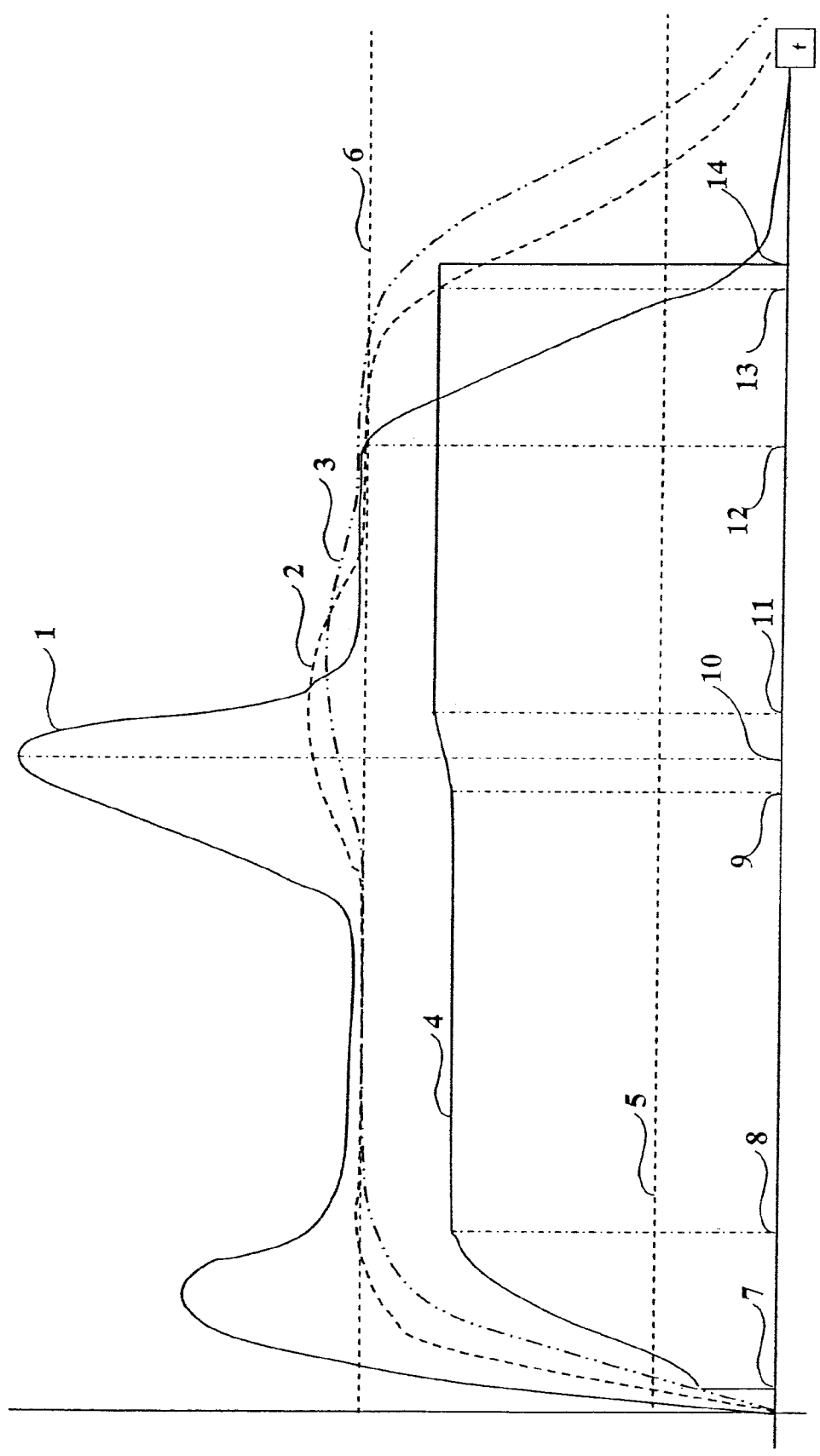

MONITORING DEVICE FOR A THERAPY DEVICE AND PROCESS

CROSS REFERENCE TO RELATED APPLICATIONS

This application is a divisional under 37 CFR 1.53(b) of pending prior application Ser. No. 11/773,042 filed Jul. 3, 2007, now abandoned which claims the priority of German Patent Application DE 10 2006 032 860.4 filed Jul. 14, 2006, the entire contents of each application are incorporated herein by reference.

FIELD OF THE INVENTION

The present invention pertains to a monitoring device for a therapy device for a patient, wherein the monitoring device has a device for determining at least one therapy parameter; and at least one alarm that can be activated for triggering an alarm when the at least one therapy parameter is below a warning limit in the activated state of the alarm as well as to a therapy device. The present invention moreover relates to a process for triggering an alarm as well as to a process for treating a patient.

BACKGROUND OF THE INVENTION

Therapy devices, for example, anesthesia devices for anesthetizing a patient, are used in practice, as a rule, in conjunction with at least one monitoring device for monitoring therapy parameters such as respiration parameters, anesthesia parameters and/or vital parameters of the patient being anesthetized.

These monitoring devices may be directly integrated within the particular therapy devices but also provided as independent, external monitoring device, and they trigger an alarm or an alarm report upon the onset of certain circumstances. The monitoring device may be designed as so-called monitors.

When such a monitoring device is used, it is common practice to preset respective limit values for the parameters to be monitored, above or below which an alarm report is triggered. These limit values, which are also called alarm limits, are usually set by the attending physician or his team, quite generally by the operator of the therapy device.

When such a monitoring device according to the state of the art are used, errors occur in alarm triggering, which may be directly or indirectly disadvantageous for the therapy being monitored or for the health and/or the well-being of the patient being treated. Such an error in alarm triggering is given, for example, when no alarm is triggered in case of an actually occurring error that should have led to an alarm (false negative alarm). This may be due to alarm limits that are set too generously or deactivated alarm limits. However, alarm reports are also sent regularly in case of anesthesia or therapy taking place properly without the development of a situation in which an alarm should have been triggered (false positive alarm, also called false alarm). This may be due to alarm limits set too strictly.

The appearance of a false negative alarm implies the great risk that the physician, who relies upon an alarm in the case of malfunction of the therapy device (for example, the anesthesia device) or in case of deviation of a parameter from its target range, detects the actually occurring error only late at best due to the absence of this alarm.

False positive alarm reports or false alarms are, by contrast, not directly hazardous to the health of the patient, but they may be indirectly hazardous. Thus, false alarms would be suitable for diverting the physician from his actual work or for preventing him from performing his work. False alarms could also be hazardous because their repeated occurrence could give reason to the physician or his team not to pay generally the necessary attention to future alarms, to generally ignore future alarms or to even deactivate the alarm means of the monitoring device in order to avoid future alarms altogether.

Such a deactivation by the physician, often intended as a temporary measure only, could regularly also occur in order to do away with a large number of false alarms, which are due in anesthesia devices, for example, to the curve usual for some forms of anesthesia, such as the slow build-up of a gaseous anesthetic during the induction of anesthesia up to a target concentration. There is later a risk in this case that one will forget to manually reactivate the alarm means. If a case of error that does require an alarm occurs in such a case, no alarm will be triggered because of the deactivation (false negative alarm), which may be associated with a safety risk for the patient. Lowering the alarm limits to a generous alarm setting to avoid false alarms will in turn increase the risk of false negative alarms, i.e., the absence of justified and necessary alarm reports.

SUMMARY OF THE INVENTION

The object of the present invention is therefore to create a monitoring device for monitoring the therapy and especially anesthesia as well as a therapy device equipped therewith and especially an anesthesia device with automatic activation of an alarm means to avoid or reduce at least false positive alarms while ensuring at the same time the greatest possible safety for the patient. The object of the present invention is, moreover, to provide a corresponding process for triggering an alarm as well as a process for the treatment and especially the anesthesia of a patient.

According to the present invention, a monitoring device is provided for a therapy device of a patient, wherein the monitoring device has means for determining at least one therapy parameter and at least one alarm means that can be activated for triggering an alarm when the at least one therapy parameter is below a warning limit in an activated state of the alarm means. The monitoring device has, furthermore, at least one means for the automatic activation of the alarm means when the at least one therapy parameter is above a lower threshold value.

The present invention will be explained below based on the example of a monitoring device for an anesthesia device for the anesthesia of a patient by means of a gaseous anesthetic, which monitoring device is likewise covered and claimed by the present invention. The monitoring device for the anesthesia device represents here any kind of monitoring device, to which the present invention is likewise applicable. Further examples according to the present invention will likewise be explained below.

When the monitoring device according to the present invention is used to monitor an anesthesia means, it has at least one means for determining at least one minimum alveolar concentration (MAC) of this gaseous anesthetic as a therapy parameter. However, if the monitoring device is intended to monitor a therapy device other than an anesthesia device, the at least one gas may also be a gas that is not used for the purpose of anesthesia but, for example, for respiration, as this will be explained below. Another parameter, for example, a concentration, a pressure, a volume, a ratio of such parameters or changes in such parameters may be determined instead of a minimum alveolar concentration in such a case.

The term "minimum alveolar concentration" is used here in agreement with its use in the pertinent literature. It denotes, within the framework of the present invention, the value of a minimal alveolar concentration of a gaseous anesthetic at which 50% of all patients no longer respond to an incision with a defense reaction. The underlying minimum alveolar concentration may be a minimum alveolar concentration (MAC) not corrected for the patient's age (called a $MAC_{40}$ value, for an approximately 40-year-old patient) or even a MAC value corrected for the age of the particular patient. It is up to the person skilled in the art to take into account alternatively the age-corrected MAC value or the $MAC_{40}$ value when carrying out the present invention. Such a determination of the MAC value may be carried out, for example, at short time intervals, e.g., every couple of milliseconds or resolved for individual breaths (for example, once per breathing cycle). The measurement may be carried out as a side-stream measurement, by means of a sample holder and using the infrared technique, or in another manner. The procedure used to determine a MAC value relative to a certain patient and a given anesthesia situation is therefore known as such to the person skilled in the art and is not the subject of the present invention.

The at least one MAC value determined by means of the monitoring device according to the present invention is a MAC value selected by the person skilled in the art. It may be an inspiratory MAC value ($MAC_{insp}$) and/or an expiratory MAC value ($MAC_{exp}$) and/or a MAC value filtered as a function of the action time of the particular gaseous anesthetic used ($MAC_{expfilt}$) of the at least one gaseous anesthetic used and/or other MAC values. If the person skilled in the art recognizes an advantage in the determination of another MAC value not expressly mentioned here or in the use of a modified MAC value, provisions are also made according to the present invention for determining and using that MAC value. It appears to the person skilled in the art from the above that provisions are also made according to the present invention for determining only one MAC value.

The determination of the MAC value may be carried out now in the inspiratory breathing gas ("inspiratory MAC value") and/or in the expiratory breathing gas ("expiratory MAC value") of the patient being anesthetized, for example, in the area of the Y-piece. The term "inspiratory MAC value" therefore pertains to a MAC value at which at least one concentration measured in the inspiration gas—especially of the at least one gaseous anesthetic used—is included, and the "expiratory MAC value" is at least one concentration from the expiration gas or the expired breathing gas, i.e., the concentration of at least one determined gas in a gas mixture.

The time that elapses until the onset of the action of the gas in question in the body is determined by calculation at least approximately in the MAC value filtered as a function of the action time of the at least one gaseous anesthetic. Various methods are known to the person skilled in the art for this filtering. The person selects the method that appears to that person to be best for the particular, given circumstances. The present invention is not bound, in its most general embodiment, to any of these filtering methods. The MAC value, which takes into account the action time, is filtered in one example for such a filtering over time that elapses between the measurement of the expiratory MAC value ($MAC_{exp}$) and the onset of the intended action in the body. Thus, in case of the use of more than only one dispensed gaseous anesthetic, the resulting MAC value can be obtained from the addition of the individual MAC values involved, which are filtered with different action time constants.

The monitoring device according to the present invention has, furthermore, an alarm means that can be activated for triggering an alarm when the at least one determined MAC value is below a warning limit or drops to a value that is at or below this warning limit in an activated state of the alarm means. This warning limit may be set as a fixed limit on the anesthesia device ("on the device side") or set by the physician or the operator of the anesthesia device in the particular case. An alarm is therefore triggered by the monitoring device only when the alarm means is activated, on the one hand, and at least one of the determined MAC values drops or has dropped below the warning limit, on the other hand.

The monitoring device according to the present invention has, moreover, a means for automatically activating the alarm means. As a basic setting, the alarm means may thus be deactivated on the device side. The automatic activation takes place when the at least one MAC value is above a lower threshold value or has risen above this value. Just like the lower warning limit, the lower threshold value may also be preset as a fixed value on the device side, but, as an alternative, it may also be set by the physician. However, it is also possible according to the present invention, for example, that the lower threshold value or even the lower warning limit is set automatically as a function of other circumstances.

The present invention is advantageously characterized in that, on the one hand, the alarm means for triggering an alarm is automatically activated only when, for example, a first phase of an anesthesia, during which most of the false alarms, especially false positive alarms, are triggered due to the slow build-up of the gaseous anesthetics or the gaseous anesthetic, has concluded and certain MAC concentrations have been reached in the inspiration or expiration gas. The appearance of false alarms as well as alarms that are triggered because certain gas concentrations could not reach or exceed a lower warning limit is advantageously prevented hereby. Consequently, the physician is also not diverted from work because no alarms have been triggered at all. For the same reason, the physician has, moreover, no motivation for deactivating the alarm means, and consequently, the physician also cannot forget to restart the alarm function or to reactivate the alarm function, which would be necessary after deactivation. The safety of the patient being anesthetized is markedly improved when the monitoring device according to the present invention is used.

The monitoring device according to the present invention is characterized, on the other hand, in that deactivation of the alarm means of the monitoring device, if such deactivation nevertheless did take place, can remain without consequence. As soon as the determined MAC value exceeds the lower threshold value, the alarm means is activated according to the present invention by itself and above all without intervention on the part of the physician or his team, i.e., automatically. The lower threshold value may be set now such that it is ensured that when this threshold value is exceeded by the at least one MAC value, for example, the above-mentioned initial phase of anesthesia is concluded with certainty. The threshold value can be set or preset generally such that when it is exceeded, phases of anesthesia during which alarm reports regularly take place without reason will have already been concluded.

Thus, provisions are made in a preferred embodiment of the monitoring device according to the present invention for the monitoring device to have a means for automatically setting the level of the lower warning limit. The warning limit is set by this means automatically when both the inspiratory MAC value, the expiratory MAC value and the expiratory MAC value of the at least one gas, which value is filtered as a function of the action time, or at least two of the values is/are at or above a lower threshold value. The value of the warning limit can be set in the particular case as a function of parameters that the person skilled in the art considers to be important or suitable.

It is thus advantageously ensured that the physician is relieved of the task of setting the lower warning limit in such a way that it is adapted to the particular case or of having to set it on the device side. This setting is performed automatically according to criteria set in advance, as soon as the three MAC values have risen to a level above a lower threshold value and it is thus ensured that a desired depth of anesthesia or phase of anesthesia is reached. In addition, one cannot forget to set the lower warning limit if it had not been set already. This is carried out rather automatically in this embodiment, and at a time at which the setting is not a reason for false alarms. It is noted that the action according to the present invention and the advantages associated herewith are also achieved if only the exceeding of the lower threshold value by any two MAC values is taken into account to set the lower warning limit instead of the exceeding of the lower threshold value by the three MAC values mentioned as examples here.

As is provided in another preferred embodiment according to the present invention, the monitoring device may have for this purpose a means for automatically setting the lower warning limit, by means of which the lower warning limit can be set at a predeterminable percentage of one of the MAC values determined to set the warning limit, for example, of the lowest of these MAC values. The percentage may be related here to a MAC value of the lowest MAC value which is averaged or filtered in another manner. It may also be related to the MAC value at the level measured last. This is left up to the person skilled in the art. An essential advantage of this embodiment is that the warning limit is set automatically and individually for the patient and the respiration parameters or MAC values thereof. Such a percentage may be, for example, above 50% of the lowest of the MAC values determined, preferably above 60%, especially preferably between 65% and 75% and especially preferably at 70%. Provisions may be made, especially in this embodiment of the present invention, for automatically adjusting the warning limit to, e.g., always 70% of the lowest MAC value in a simple manner, and a resetting of the warning limit to always higher values than before—but not to lower values than before—is preferred. On the one hand, this percentage guarantees the safety of the anesthesia for the patient, and, on the other hand, the distance between the warning limit and the determined MAC values is sufficiently great to avoid false alarms.

Yet another, likewise preferred embodiment according to the present invention is characterized in that it has a means for setting a maximum value for the lower warning limit. An advantage of this embodiment according to the present invention is that there is no premature alarm in case of declining MAC values because of a lower warning limit set automatically or independently unrealistically high. The lower warning limit could be set at such an undesirably high value, for example, due to instantaneous freak values of the MAC value(s) being considered in the upward direction, which are, however, not typical for this value in the time curve of the MAC values. This also applies to an instantaneous, especially initial rise in the concentration of a gaseous anesthetic intended by the physician for the purpose of more rapid build-up. The above-described average, which is proposed as a possibility, or filtration according to another method, is not absolutely necessary by means of this embodiment according to the present invention when setting the percentage. This advantageously leads to a simplification of the design of the monitoring device according to the present invention.

In another, likewise preferred embodiment according to the present invention, the monitoring device has a means for filtering the inspiratory MAC value over time or over a time interval. It can be advantageously ensured hereby, in general, that individual MAC values of a MAC value, which are excessively high or too low (so-called freak values), will not lead to the setting of the lower warning limit, nor will they essentially co-determine the setting of these values, because such a setting based on freak values does not lead to the setting of a warning limit at the actually intended level. Therefore, this embodiment according to the present invention has the advantage of increased process safety. Such a filtering may be based, for example, on a mean value method or a mean value method with sliding average (for example, over 30-sec periods). Any other method known to the person skilled in the art, which can contribute, as was described above, to greater precision and/or to an increase in process safety, should likewise be considered to be covered by the present invention. Such a means may, of course, also be provided according to the present invention for filtering over time for the MAC value filtered as a function of the action time regardless of any further or additional filtering of this MAC value.

The alarm means of the monitoring device of another preferred embodiment is suitable and set up to trigger an alarm whose intensity increases over time. The alarm therefore begins quietly and initially disturbs the persons present in their work less than at a later point in time. Thus, the persons present do not fail to see and/or hear an alarm, on the one hand, and, on the other hand, it is not necessary to interrupt any activity immediately upon the onset of the alarm in order to end the alarm immediately. This is pleasant and above all advantageous above all when the physician or the attending therapist must walk only a few steps to the patient or the anesthesia device and an alarm that is already very intense initially would otherwise needlessly burden the persons present until they reach the anesthesia device. An alarm that is more intense from the very beginning would not "alarm" the person in charge "more" but would only be more unpleasant for all persons concerned. In addition, in case of a gradually increasing intensity, a physician, who is still performing other tasks in the meantime, can also assess the urgency of the alarm and whether he can still conclude the work just being performed before he addresses those circumstances triggering the alarm. The time elapsing until the alarm is increased (i.e., until its intensity increases) can be selected to be such that the alarm is intensified at the latest after the end of a time that corresponds to 50% of the time constant of the fastest gas present in the gas mixture (i.e., the gas with the shortest time constant). This consequently generates an alarm in time before the unintended waking up of the patient.

The monitoring device may also have for this purpose a means for calculating when a MAC value will foreseeably drop below the warning limit, in which case the result of this calculation can be displayed in a suitable manner. This is advantageous especially when therapeutic measures taken by the physician and the triggering of the alarm more or less overlap. A look at the result of the calculation can already represent the feedback to the physician to determine whether or not the measures he was taking in the meantime (such as an increase in the concentration of an anesthetic) will suffice, based on experience, to avoid a relevant violation of the warning limit and whether the alarm is "self-limiting" due to waiting briefly based on the measures already taken and will come to an end without his intervention.

In yet another preferred embodiment according to the present invention, the monitoring device has a means for setting and/or correcting the lower warning limit in case of changes in the set values for the anesthesia on the anesthesia device. When the physician has made changes, for example, in the respiration parameters or in the level of the anesthetic concentration administered, it may become necessary hereby to change (raise or lower) the lower warning limit. The advantage of this embodiment according to the present invention is that the warning limit is automatically adapted to the changed circumstances by means of the setting and/or correcting means. Avoidable alarms, which do not provide the physician with any additional information, are advantageously avoided hereby. This resetting or correction may be taken into account, for example, by means of a model calculation.

In yet another preferred embodiment according to the present invention, the monitoring device has a means for deactivating the alarm means. Deactivation of the alarm means can be carried out by the deactivation means when at least one MAC value taken into account for setting the warning limit assumes a value lower than or equal to the lower threshold value. This deactivation may take place automatically or be triggered by the user. An advantage associated herewith is that the monitoring device is put into an initial state from which the lower warning limit is reset to a current value each time the MAC value rises again above the lower threshold value. Moreover, there are no meaningless alarms, for example, at the end of the anesthesia because of the value dropping below the warning limit, without the physician himself having to perform deactivation of the warning limit. If the setting parameters, which determine the MAC values, are known in the system, a necessary deactivation of the alarm system or of the warning limit can be deduced, i.e., implemented, in time from the change in the setting of these MAC values.

In yet another preferred embodiment according to the present invention, the monitoring device has means for determining at least one MAC value as discussed above. However, unlike in the case discussed above, the means for determining MAC values are suitable and intended for determining MAC values of different gases and especially different gaseous anesthetics. By means of another means or the same means of this embodiment, a total MAC value can be determined from the determined MAC values of the different gases. The total MAC value is used as the basis for monitoring the anesthesia device essentially as was described above.

For example, in the case of an anesthetic gas mixture comprising $N_2O$ and isoflurane, the $MAC_{exp}$ determined for $N_2O$ is filtered with a different action time (action time for $N_2O$) than the $MAC_{exp}$ determined for isoflurane (action time for isoflurane). The two MAC values, thus filtered, are added to obtain $MAC_{expfilt}$, and volume weighting or any other suitable weighting may be performed between these two gases. A relatively accurate picture of the actions of the gas mixture on the patient is thus obtained.

Another preferred embodiment is characterized in that it has a means for the automatic activation of the alarm means when the lowest determined MAC value or the lowest of the determined MAC values is above the threshold value and the inspiratory MAC value, $MAC_{insp}$, is at the same time higher than the expiratory MAC value, $MAC_{exp}$. Provisions are made in yet another preferred embodiment for the alarm limit to be activated automatically when the inspiratory MAC value, $MAC_{insp}$, is higher than the determined percentage (for example, 40%, 50%, 60%, 70%, 80% or 90%) of the expiratory MAC value filtered as a function of the action time of the breathing gas, $MAC_{expfilt}$, a value higher than 80% being especially preferred.

These embodiments according to the present invention are advantageously characterized in that based on the additional requirement, namely, that the inspiratory MAC value must be higher than the expiratory MAC value or than a percentage of the MAC value filtered as a function of the action time of the breathing gas before the alarm limit is set, it is ensured that the anesthesia system rather than the patient is the "source" of the measured concentration of the at least one gas. In other words, this means that a first-time activation—or an increase—in the lower warning limit takes place only when the anesthesia is at an early stage (i.e., at its beginning) and it is also meaningful and desired to set the warning limit. The MAC value measured in the inspiratory breathing gas is higher than the MAC value measured in the expiratory breathing gas at this stage. The situation is different at a later stage of anesthesia (i.e., by its intended end): The inspiratory MAC value is lower here than the expiratory MAC value, because the patient breathes out more gaseous anesthetic than is supplied to him. It is no longer desirable to raise the alarm limit at this stage. The same action is also given when the inspiratory MAC value is measured at a percentage of the expiratory MAC value filtered as a function of the action time of the breathing gas. Thus, both cases contribute to the avoidance of the setting of the lower warning limit, which is undesired because it is false, and of alarms falsely triggered hereby.

The object according to the present invention is also accomplished by a therapy device. It is accomplished, furthermore, by a process for triggering an alarm as well as by a process for treating a patient. The advantages achieved hereby correspond in full measure to the advantages discussed above. To avoid repetitions, reference is expressly made to the above discussion of these advantages. It is pointed out that all the device features that can be found in this description of the present invention are also the subject of the corresponding processes according to the present invention. Furthermore, it is pointed out that a further aspect of the present invention pertains not only to therapy devices such as anesthesia devices, but also to other therapy devices if the person skilled in the art recognizes that the application of the basic idea of the present invention can also be extrapolated to and/or is advantageous for this device. This also applies to the processes. They are not directed solely towards the treatment, for example, anesthesia, or the respiration of a patient, but also to other applications obvious to the person skilled in the art.

The present invention was described based on the example of anesthesia as well as a monitoring device as well as an anesthesia device used in this connection. The essential basis was the MAC value here. However, it is obvious to the person skilled in the art that the present invention and each of its partial aspects, variants and/or features can also be readily extrapolated to a monitoring device (monitoring means) for other therapy devices, in which automatic activation of an alarm means is intended.

Such therapy devices also comprise, among other things, respirators. The explanations given above in connection with MAC values are extrapolated for this to volume, pressure or concentrations as well as ratios or changes of the gases used in the process: Such an other therapy device is, for example, a device for monitoring a respiratory minute volume to be administered. If the respiration of a patient is supported by a respiration ventilator by means of this device (intensive care, home care, anesthesia respiration), the ventilator can automatically increase the percentage of the mandatorily administered respiratory volume, for example, on the basis of certain values preset by the user (minimal respiratory minute volume, $CO_2$ values, hemodynamic parameters or the like) in proportion to the volume from the patient's spontaneous respiratory activity. This increase can take place in a regulated or controlled manner. The risk of insufficient respiration of the patient increases now, should this mandatory respiration be suddenly eliminated, e.g., due to a technical failure. Corresponding to the process according to the present invention as well as in case of the use of a means designed according to the present invention, automatic activation of a lower warning limit for the respiratory minute volume to be supplied by the therapy device can take place in anticipation. The warning limit can now be correspondingly adapted automatically to values which are to be monitored and amount, for example, at least to about 70% of the mandatory respiratory minute volume. Provisions could be made according to the present invention for the warning limit to be raised only but not lowered automatically. If the percentage of respiratory minute volume mandatorily supplied by the machine then drops below the automatically activated warning limit (due to failure of the ventilator, leakages or the like), a corresponding alarm is triggered. The at least one MAC value mentioned in the description given above as well as the appended patent claims corresponds at least to a minimal respiratory minute volume, a $CO_2$ value, a hemodynamic parameter or the like in case of the device being described here for monitoring a respiratory minute volume to be administered. The above-mentioned MAC values are to be complemented here by parameters such as minimal respiratory minute volumes, $CO_2$ values, hemodynamic parameters or the like as well as any combinations hereof.

Another example of such other therapy devices is a device for monitoring a pressure to be applied: So-called heart-lung machines, with which oxygenation of the patient's blood is guaranteed during the surgical procedure, are regularly used in connection with cardiac surgery. The lung does not contribute to the oxygenation now. It is also usually not respirated and therefore also not monitored.

However, it is frequently necessary to prevent the lung(s) from collapsing by applying a constant pressure. If the patient's respiration pressure is measured during such an operation, an alarm system, which correspondingly triggers an alarm when the previously prevailing respiration pressure drops, can be automatically activated according to the present invention. The lower warning limit may be set, for example, at 75% of the respiration pressure mean value of the last 60 sec and is automatically increased only, but it cannot be lowered, so that an alarm would be triggered should the value drop below the limit.

The present invention will be described in detail below on the basis of an exemplary embodiment with reference to the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

In the drawings:

FIG. 1 is a graph showing the course of MAC during anesthesia over the time t.

DESCRIPTION OF THE PREFERRED EMBODIMENT

Referring to the drawings in particular, the conditions corresponding to MAC values at the beginning of an anesthesia are shown at the left-hand edge of the graphic view in FIG. 1. It can be recognized from FIG. 1 that the inspiratory MAC value, $MAC_{insp}$ (the corresponding curve is designated by 1 and is drawn as a solid line), is raised rapidly to a prominent level for the purpose of rapidly inducing anesthesia. The expiratory MAC value, MAC, (the corresponding curve is designated by 2 and is drawn as a broken line), also increases with a time delay. The expiratory MAC value, $MAC_{exfilt}$ (the corresponding curve is designated by reference number 3 and is drawn as a two-dot broken line), which is filtered as a function of its action beyond the blood-brain barrier, rises with an even longer delay.

The monitoring device of the anesthesia device, by means of which the schematic curves in FIG. 1 were generated, has been set such that a lower warning limit $MAC_{lowtrsh}$ (designated by reference number 4) is activated or set only when all three MAC values 1, 2 and 3 exceed a lower threshold value 5. This happens at time 7 in FIG. 1. The lower warning limit 4 is seen here in the example according to FIG. 1 at about 70% of the lowest of the three MAC values 1, 2 and 3, i.e., at 70% of MAC value 3. The lower threshold value 5 may be set, for example, at 0.3 MAC. Presetting a comparatively low lower threshold value 5 is meaningful, e.g., in case of a balanced anesthesia with additional intravenous administration of anesthetics, because this entire invention can, of course, be used advantageously in each embodiment for balanced anesthesia as well.

Based on the further rise of the values 1, 2 and 3 (i.e., of the values $MAC_{insp}$, $MAC_{exp}$ and $MAC_{exfilt}$), the lower warning limit 4 ($MAC_{lowtrsh}$) rises between the points in time 7 and 8 to a level that remains constant between the points in time 8 and 9. Due to the repeated rise of the inspiratory MAC value 1 with a peak at time 10, the values 2 and 3 will also rise, again with a time delay, as a result of which the lower warning limit 4 will also rise slightly between the points in time 9 and 10, following the lowest of the three MAC values determined.

Line 6 (which indicates the value $MAC_{lowtrsh-max}$), which is also shown in FIG. 1, indicates a preset maximum for the automatic increase of the lower warning limit 4. This is an upper limit set prior to the anesthesia for the lower warning limit 4, which is, however, not reached by the lower warning limit 4 in the example shown in FIG. 1.

A drop of the inspiratory MAC value 1, which is also followed by a lowering of the MAC values 2 as well as 3 with a time delay, can be recognized beginning from the time 12 in FIG. 1. Since not only the MAC value 1 but also the MAC value 2 have dropped below the lower warning limit 4 at time 13, the conditions for triggering an alarm are met for the monitoring device according to this embodiment (the drop of a MAC value below the warning limit 4 may already be sufficient for triggering an alarm in other embodiments). The monitoring device therefore triggers an alarm between the points in time 13 and 14.

Since two MAC values (here: the MAC values 1 and 2) have already assumed values below the lower threshold value 5 at the time of the alarm at time 13, the physician is asked by means of a dialogue field whether the alarm device could be deactivated, for example, because the end of anesthesia is intended. The physician answered this with a "yes" at time 14, after which the lower warning limit 4 drops to its initial value and the alarm system is thus deactivated. If $MAC_{exp}$ is higher than $MAC_{insp}$, this is also an indicator for the end of anesthesia, so that the alarm system can be deactivated upon a "yes" answer from the therapist or upon approval by the therapist.

It is pointed out that an upper warning limit may, of course, also be provided besides the lower warning limit in each embodiment. All the statements made above concerning the setting of the lower warning limit also apply now to the upper warning limit and can be extrapolated to this if considered by the person skilled in the art to be meaningful.

The taking into account of all three of the MAC values or of the relation thereof to activate the alarm means, as in FIG. 1, advantageously ensures that an anesthesia device monitored by means of the monitoring device is, indeed, also the cause of the anesthesia with a corresponding depth of anesthesia, i.e., that the patient's anesthesia can be attributed to the gaseous anesthetics being monitored. This information is essentially attached to the inspiratory MAC value 1.

If the expiratory MAC value 2 is, moreover, also required to exceed the lower threshold value 5, as in this preferred embodiment according to FIG. 1, this increases the safety of the process further due to the fact that a time shift between the reaching of an inspiratory concentration and the same concentration in the expiratory breathing gas due to diffusion processes and shifts between compartments of the body is taken into account, which contributes to a more precise information on the anesthesia.

If, moreover, the means for automatically setting the lower warning limit 4 of the monitoring device also takes into account the value of the MAC value 3 of the at least one gaseous anesthetic, which is filtered as a function of the action time, or the exceeding of the lower threshold value 5 by this MAC value 3 in case of activation of the alarm means, the action of the gaseous anesthetic being used on cerebral processes is additionally taken into account. The expiratory MAC value 3 filtered as a function of the action time is to be defined as an indicator of the depth of anesthesia, and it takes into account the passage of the gaseous anesthetic being used through the blood-brain barrier, as was already explained above. Thus, it is a more precise parameter of anesthesia than $MAC_{exp}$ alone. It is expressly pointed out that FIG. 1 shows the case in which only one gaseous anesthetic is used. In the case discussed in detail above, in which not only one gas but a gas mixture is used, the total $MAC_{expfilt}$, filtered as a function of the individual action times of the particular individual gases involved, replaces the MAC value 3 according to FIG. 1. Furthermore, a total $MAC_{insp}$ and a total $MAC_{exp}$ can replace the MAC values 1 and 2.

It applies to the means used to carry out the present invention that a means can definitely also perform different tasks. Thus, a means for, e.g., determining MAC values and at the time for setting the lower warning limit and/or additional functions may be able to be used.

Provisions are also made according to the present invention for working with more than only one lower warning limit. Thus, the person skilled in the art may provide different warning limits for different MAC values, and a plurality of means are used to determine them, set them, etc. Each of these warning limits may be designed as explained above.

Moreover, it is obvious to the person skilled in the art that a combination of the determination of at least one MAC value and the determination of at least one additional variable, which is not a MAC value, is possible in each embodiment of the present invention. Such an additional variable may be, for example, a volume, a volume flow, a pressure or the like. It is thus possible according to the present invention especially to set the lower warning limit, taking into account at least one MAC value and at least one other variable. It is obvious in this connection that when different variables (for example, a MAC value and a volume value) are determined and used, it is also possible to take into account different lower threshold values (a threshold value for the MAC value and another for the volume value), which must each be exceeded in order to set the lower warning limit.

The present invention proposes a monitoring device for monitoring a therapy device, for example, an anesthesia device or respirator, by means of which an alarm means for triggering an alarm when the value drops below a lower warning limit is automatically activated when at least one determined therapy parameter drops below this lower warning limit 4. The lower warning limit (warning limit) is first set automatically in this case. In addition, a therapy device monitored by means of the monitoring device according to the present invention and especially an anesthesia device as well as a respirator are proposed. The present invention proposes, furthermore, a process for triggering an alarm as well as a process for treating a patient.

While specific embodiments of the invention have been shown and described in detail to illustrate the application of the principles of the invention, it will be understood that the invention may be embodied otherwise without departing from such principles.

What is claimed is:

1. A process, comprising the steps of:
   determining one or more minimum alveolar concentration (MAC) values of at least one gas during an anesthesia process wherein said one or more MAC values comprises one or more of an inspiratory MAC value, an expiratory MAC value, a MAC value filtered as a function of a reaction time and another MAC value of the least one gas;
   filtering said one or more MAC values over a period of time;
   automatically setting a lower and/or upper warning limit when said one of said one or more MAC values is greater than a lower threshold value,
   wherein said lower and/or upper warning limit are based on a predetermined percentage of lowest and/or highest values of said one or more MAC values;
   providing at least one activatable alarm device;
   providing an automatic activation device;
   activating said at least one activatable alarm device from a non-activated state to an activated state via said automatic activation device when said one or more MAC values is greater than the lower threshold value; and
   sending an alarm with said at least one activatable alarm device in said activated state when said one or more MAC values is less than the lower warning limit or greater than the upper warning limit.

2. A process in accordance with claim 1, wherein at least one of a maximum value is determined for the lower warning limit and a minimum value is determined for the upper warning limit.

3. A process in accordance with claim 1, wherein at least one filtering of the at least one or more MAC values is done by means of a sliding mean value.

4. A process in accordance with claim 1, wherein changes in set values are taken into consideration via a model calculation for one or more of setting and correcting the one of the lower warning limit and the upper warning limit.

5. A process in accordance with claim 1, wherein the alarm device is triggered when the inspiratory MAC value and the expiratory MAC value fall below the threshold value.

6. A process in accordance with claim 1, wherein the alarm takes place with an intensity increasing over time and/or a point in time is calculated, at which the MAC value filtered depending on the reaction time will fall below the lower threshold value, said alarm device being deactivated when at least one value taken into consideration for setting the warning limit assumes a value that is equal to or less than the lower threshold value.

7. A process in accordance with claim 1, wherein, when two or more gases are used, an alarm time point is calculated depending on a reaction time constant of a respective fastest acting gas.

8. A process in accordance with claim 1, further comprising the steps of:
   determining at least one MAC value of each gas when two or more gases are used; and
   determining a respective corresponding total MAC value.

9. A process, comprising the steps of:
   determining one or more minimum alveolar concentration (MAC) values of at least one gas during a supply of breathing gas to the patient;
   filtering said one or more MAC values over a period of time;
   automatically setting a warning limit based on said one or more MAC values when said one or more MAC values is greater than a lower threshold value;
   providing at least one activatable alarm element;
   providing an automatic activation element for switching said activatable alarm element from a non-activated to an activated state;
   activating said at least one activatable alarm element from said non-activated state to said activated state via said automatic activation element when said one or more MAC values is greater than the lower threshold value; and
   providing an alarm as output via said at least one activatable alarm element after activating said at least one activatable alarm element to said activated state when said one or more MAC values is one of greater than an upper warning limit and less than a lower warning limit.

10. A process in accordance with claim 9, wherein said warning limit is automatically set based on a predetermined percentage of one of lowest values of said one or more MAC values and highest values of said one or MAC values, said one or more MAC values comprising one or more of an inspiratory MAC value, an expiratory MAC value, a MAC value filtered as a function of a reaction time and another MAC value of the least one gas.

* * * * *